United States Patent
Teoh

(10) Patent No.: US 9,687,633 B2
(45) Date of Patent: Jun. 27, 2017

(54) SAFETY NEEDLE DEVICES AND RELATED METHODS

(71) Applicant: B. BRAUN MELSUNGEN AG, Melsungen (DE)

(72) Inventor: Hui Kuun Teoh, Penang (MY)

(73) Assignee: B. Braun Melsungen AG, Melsungen (DE)

( * ) Notice: Subject to any disclaimer, the term of this patent is extended or adjusted under 35 U.S.C. 154(b) by 182 days.

(21) Appl. No.: 14/540,330

(22) Filed: Nov. 13, 2014

(65) Prior Publication Data

US 2015/0151086 A1    Jun. 4, 2015

Related U.S. Application Data

(60) Provisional application No. 61/911,896, filed on Dec. 4, 2013.

(51) Int. Cl.
*A61M 5/00* (2006.01)
*A61M 25/06* (2006.01)
*A61M 5/32* (2006.01)

(52) U.S. Cl.
CPC .... *A61M 25/0618* (2013.01); *A61M 25/0612* (2013.01); *A61M 5/3273* (2013.01); *A61M 2005/325* (2013.01); *A61M 2005/3249* (2013.01); *Y10T 29/49826* (2015.01)

(58) Field of Classification Search
CPC .......... A61M 25/0097; A61M 25/0606; A61M 39/0693; A61M 39/221; A61M 39/0606; A61M 2005/325; A61M 2005/3249; A61M 5/0618; A61M 5/0612
USPC ...................................................... 604/263
See application file for complete search history.

(56) References Cited

U.S. PATENT DOCUMENTS

| | | |
|---|---|---|
| 8,038,647 B2 | 10/2011 | Harding et al. |
| 8,257,313 B2 | 9/2012 | McKinnon et al. |
| 8,257,322 B2 * | 9/2012 | Koehler .............. A61M 5/1626 604/263 |
| 8,273,056 B2 | 9/2012 | Kuracina et al. |
| 8,486,024 B2 | 7/2013 | Steube |
| 8,628,497 B2 | 1/2014 | Finnestad et al. |
| 8,672,895 B2 | 3/2014 | Kuracina et al. |
| 8,715,250 B2 | 5/2014 | Tremblay |
| 8,764,711 B2 | 7/2014 | Kuracina et al. |
| 8,821,439 B2 | 9/2014 | Kuracina et al. |
| 8,834,422 B2 | 9/2014 | Walker et al. |
| 8,926,563 B2 | 1/2015 | Steube |
| 8,939,938 B2 | 1/2015 | Funamura et al. |
| 9,238,104 B2 | 1/2016 | Kuracina et al. |
| 9,375,552 B2 | 6/2016 | Tremblay |

(Continued)

*Primary Examiner* — Edelmira Bosques
(74) *Attorney, Agent, or Firm* — Klein, O'Neill & Singh, LLP

(57) ABSTRACT

A needle safety device is disclosed in which a needle guard has several biasing arms that are biased by the needle shaft in a ready to use position. But in a protective position, at least one of the biasing arms is no longer biased by the needle shaft and moves to block a distal opening of the needle guard. The needle has a change in profile for engaging an opening on a proximal wall in a protective position. The needle guard may be formed from a stamped metal sheet having a plurality of cuts or clits. A catheter hub with a catheter tube can further be added for a safety catheter assembly.

10 Claims, 6 Drawing Sheets

(56) References Cited

U.S. PATENT DOCUMENTS 9,399,119 B2     7/2016    Kuracina et al.
9,440,052 B2     9/2016    Kuracina et al.

* cited by examiner

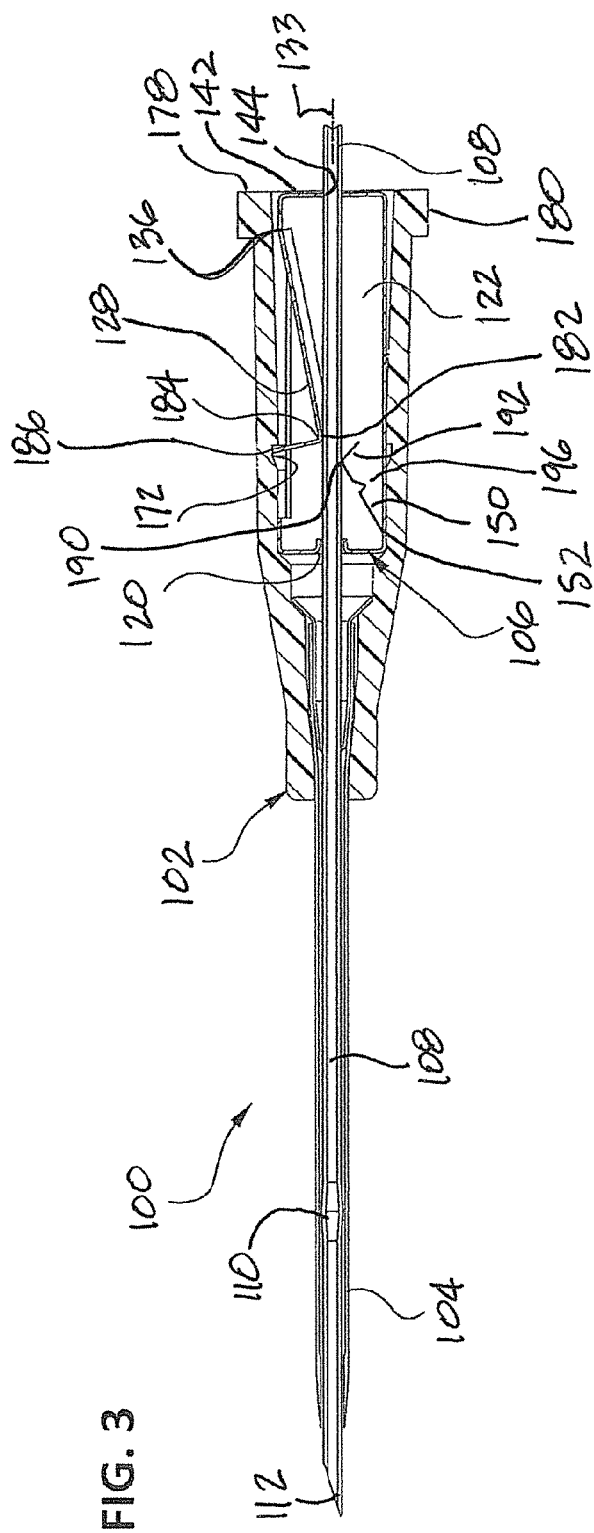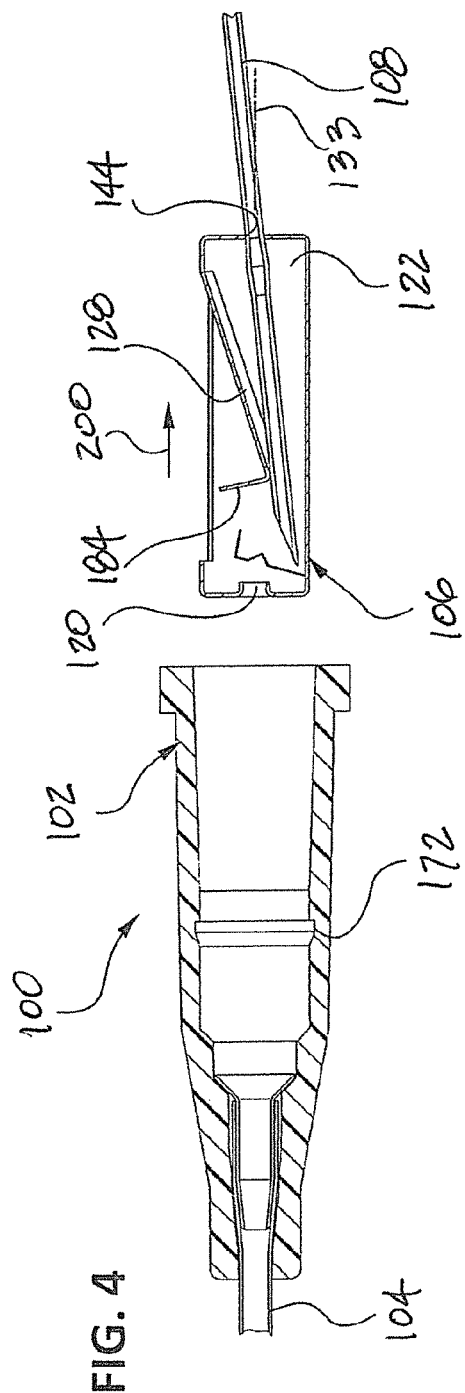
FIG. 3
FIG. 4

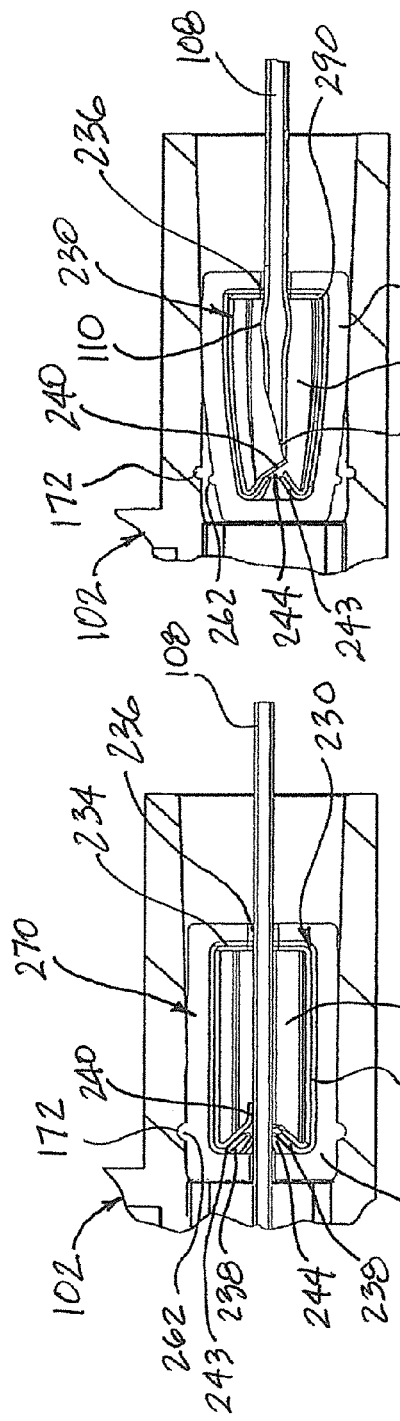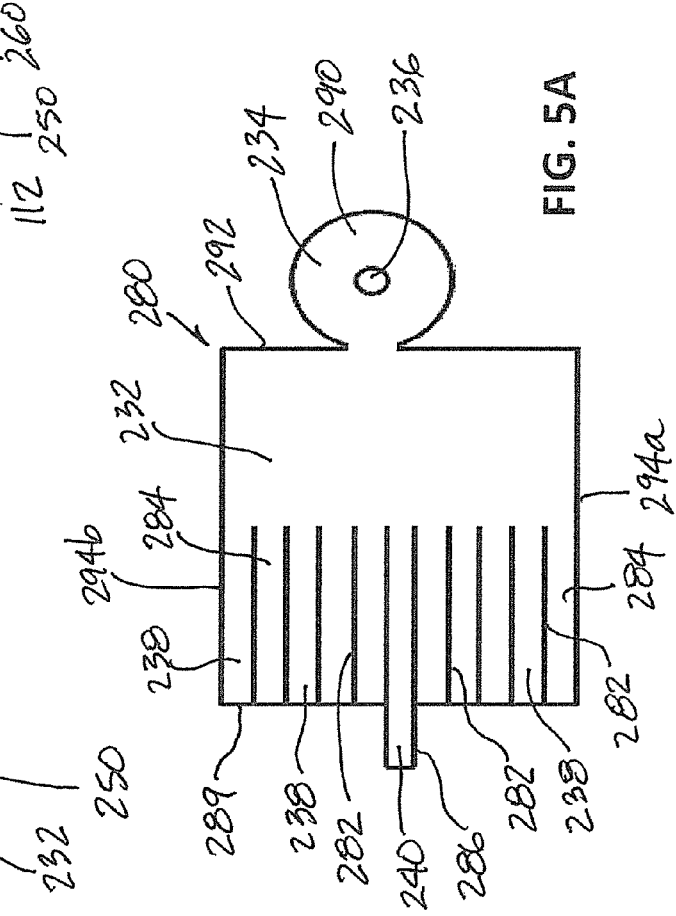

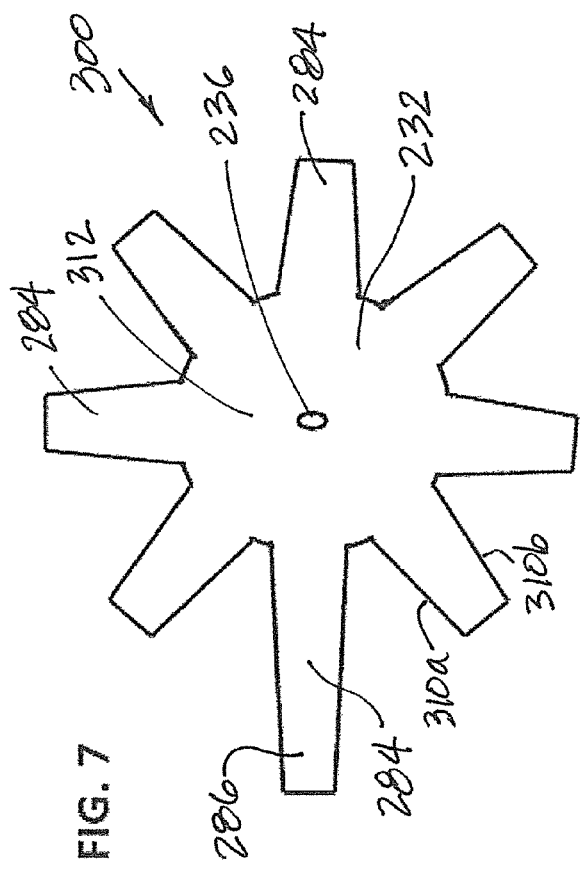
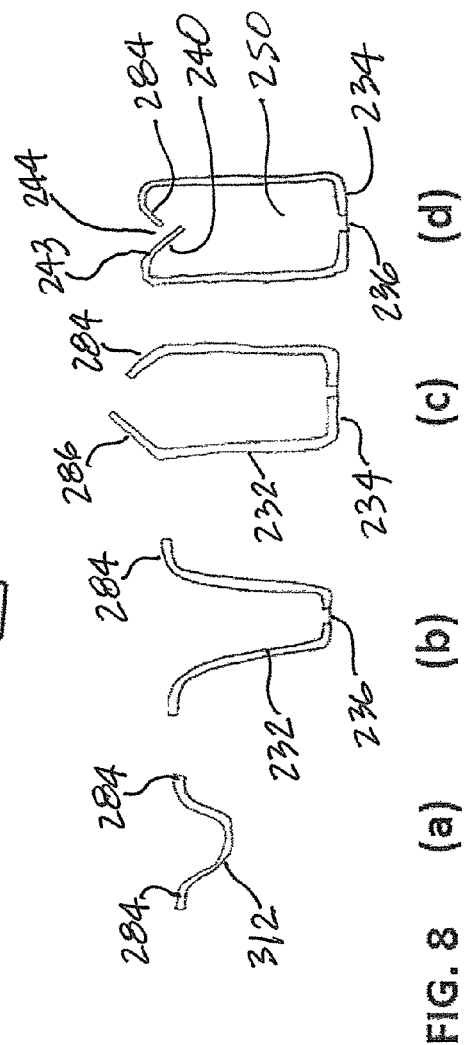
FIG. 7
FIG. 8

SAFETY NEEDLE DEVICES AND RELATED METHODS

FIELD OF ART

This invention relates generally to needle safety devices, systems, and methods wherein a needle tip is covered from inadvertent needle sticks following use. More specifically, the present disclosure relates to catheter devices involving a passive needle guard that automatically covers a needle tip during removal of a needle following successful venipuncture and methods for using and making said devices.

BACKGROUND

Hypodermic needles are notorious for spreading bloodborne diseases such as Hepatitis B, Hepatitis C, and Human Immunodeficiency Virus ("HIV"), the virus that causes Autoimmune Deficiency Syndrome ("AIDS"). Health care workers are among those most at risk for contracting such diseases, as hypodermic needles are commonly used in medical fields. Needle stick injuries may arise during planned use and exposure, and/or as a result of carelessly or maliciously discarded needles.

Of particular concerns are injuries from hollow-bore needles, especially those used for blood collection or intravenous ("IV") catheter insertion. These devices are likely to contain residual blood and are associated with an increased risk for HIV transmission. Additionally, devices that require manipulation or disassembly after use, such as hollow-bore needles used for IV catheter insertion, have rates of injury over five times that for disposable hypodermic syringes. Such injuries most often occur during or after use and before disposal of the used needle.

IV catheters are traditionally used to infuse fluids, such as saline solution, various medicaments, and/or total parenteral nutrition into a patient. Such catheters may also be used to withdraw blood from a patient, and/or monitor various parameters of the patient's vascular system.

To introduce an IV catheter into a patient, an over-the-needle catheter may be mounted over a hollow-bore introducer needle having a sharp distal tip. The inner surface of the catheter may tightly engage the outer surface of the needle to prevent catheter peel back and facilitate insertion of the catheter into a blood vessel. The tip of the introducer needle may extend beyond the distal tip of the catheter tube to enable insertion of the catheter at a shallow angle through the patient's skin and into a blood vessel.

To verify proper placement of the needle and catheter in the blood vessel, the clinician may confirm the presence of blood "flashback" in a flashback chamber associated with the catheter and needle assembly. Once proper placement is confirmed, the clinician may then apply pressure to the blood vessel to occlude the vessel, thereby minimizing further blood flow through the introducer needle and catheter. The clinician must then withdraw the needle from the catheter to enable continued access to the blood vessel through the catheter. This process of physically manipulating and disassembling the needle and catheter after the catheter has been properly positioned creates substantial risks of accidental needle sticks and exposure to blood and blood-borne pathogens.

SUMMARY

Aspects of the present disclosure are directed to a needle safety device comprising a needle connected to a needle hub, said needle comprising a needle shaft and a change in profile near a needle tip; and a needle guard having a body defining an interior cavity, a distal wall having a distal opening, and a proximal wall having a proximal opening having the needle shaft passing through both the distal opening and the proximal opening in a ready to use position in which the needle tip is exposed; wherein the change in profile has a larger cross-sectional dimension than a dimension of the proximal opening for engaging the proximal opening in a protective position; wherein the needle guard comprises at least two biasing members and wherein at least one of the two biasing members has a first position when the needle tip is exposed and a second position when the needle tip is located inside the interior cavity of the needle guard; and wherein in the first position the at least one of the two biasing members is biased by the needle shaft and wherein in the second position the at least one of the two biasing members is not biased by the needle shaft and covers at least part of the distal opening of the distal wall to prevent the needle tip from re-emerging out the distal opening.

A further aspect of the device wherein the at least one of the two biasing members can include an intermediate bent section.

A further aspect of the device wherein the at least one of the two biasing members that covers at least part of the distal opening can include a V-shape, an N-shape, or other shaped bent section or sections to reduce surface contact with the needle.

The device can further comprise a catheter hub and a catheter tube and wherein the needle guard can be located in an interior cavity or exterior of the catheter hub.

The device wherein the bent section can have a V-shape.

The device wherein the at least two biasing members can comprise a first biasing arm and a second biasing arm and wherein the first biasing arm can have a fixed end near the proximal wall and the second biasing arm can have a fixed end near the distal wall.

The device wherein the distal opening can embody a dynamic opening that changes size depending on the position of the needle shaft.

The device wherein the distal opening can be circumscribed or defined by a plurality of independently movable fingers.

The device wherein the at least two biasing members can comprise a first biasing arm and a second biasing arm and wherein the first biasing arm can have a free end that points at the distal wall and the second biasing arm can have a free end that points at the proximal wall.

The device wherein the needle guard can be rolled from a stamped metal sheet and wherein the stamped metal sheet has a plurality of cuts or slits for forming the biasing members.

A further aspect of the present disclosure is a needle guard that can be made from plastic or at least partly from plastic. Alternatively, the guard can be formed from a stamped metal sheet and then rolled or drawn against one or more dies to form at least part of the shape of the guard. The guard may include a welded seam or devoid of any welding.

A further aspect of the present disclosure includes a method of manufacturing a needle safety device. The method can comprise the steps: forming a needle with a needle shaft and a change in profile near a needle tip; attaching the needle shaft to a needle hub; forming a needle guard from a stamped metal sheet having a body with a plurality of cuts or slits by rolling that body to form a guard body with an interior cavity, a distal wall having a distal opening, and a proximal wall having a proximal opening;

placing the needle shaft through both the distal opening and the proximal opening in a ready to use position in which the needle tip is exposed. The needle can also be assembled by having the cannula passing through the needle guard from the blunt back end of the cannula opposite the needle tip before the cannula is glued to the cannula hub. This will ensure the sharpness of the cannula, such as not accidentally bending against a surface. Wherein the change in profile has a larger cross-sectional dimension than a dimension of the proximal opening for engaging the proximal opening in a protective position; wherein the needle guard comprises at least two biasing members and wherein at least one of the two biasing members has a first position when the needle tip is exposed and a second position when the needle tip is located inside the interior cavity of the needle guard; and wherein in the first position the at least one of the two biasing members is biased by the needle shaft and wherein in the second position the at least one of the two biasing members is not biased by the needle shaft and covers at least part of the distal opening of the distal wall to prevent the needle tip from re-emerging out the distal opening.

The method can further comprise the step of forming a catheter hub and a catheter tube and placing the needle through the catheter tube.

The method can further comprise the step of placing the needle guard into an interior cavity of the catheter hub.

The method can further comprise the step of engaging a projection on the needle guard with a guard engagement section in the interior cavity of the catheter hub.

The method wherein the at least two biasing members can comprise a first biasing arm and a second biasing arm and wherein the first biasing arm can have a fixed end near the proximal wall and the second biasing arm can have a fixed end near the distal wall.

The method wherein the distal opening can be circumscribed or defined by a plurality of independently movable fingers.

BRIEF DESCRIPTION OF THE DRAWINGS

These and other features and advantages of the present device, system, and method will become appreciated as the same becomes better understood with reference to the specification, claims and appended drawings wherein:

FIG. 3 is a cross-sectional view of a safety device integrated into an intravenous catheter assembly in accordance with the present disclosure;

FIG. 4 is a cross-sectional view of the intravenous catheter assembly of FIG. 3 illustrating retraction of the needle through the distal opening into the hollow interior region of the needle guard;

FIG. 5 is a close up cross section view of another embodiment of the needle guard;

FIG. 5A is a plan view of a stamped metal sheet usable to form the needle guard of FIG. 5;

FIG. 6 is a cross section view of the needle guard of FIG. 5 in a protective position;

FIG. 7 is a plan view of an alternative stamped metal sheet usable to form the needle guard of FIG. 5;

FIG. 8(a)-(d) are schematic views of a drawing process for forming a needle guard using the stamped metal sheet of FIG. 7;

DETAILED DESCRIPTION

The detailed description set forth below in connection with the appended drawings is intended as a description of the presently preferred embodiments of safety needle assemblies provided in accordance with aspects of the present devices, systems, and methods and is not intended to represent the only forms in which the present devices, systems, and methods may be constructed or utilized. The description sets forth the features and the steps for constructing and using the embodiments of the present devices, systems, and methods in connection with the illustrated embodiments. It is to be understood, however, that the same or equivalent functions and structures may be accomplished by different embodiments that are also intended to be encompassed within the spirit and scope of the present disclosure. As denoted elsewhere herein, like element numbers are intended to indicate like or similar elements or features.

Figure 1:
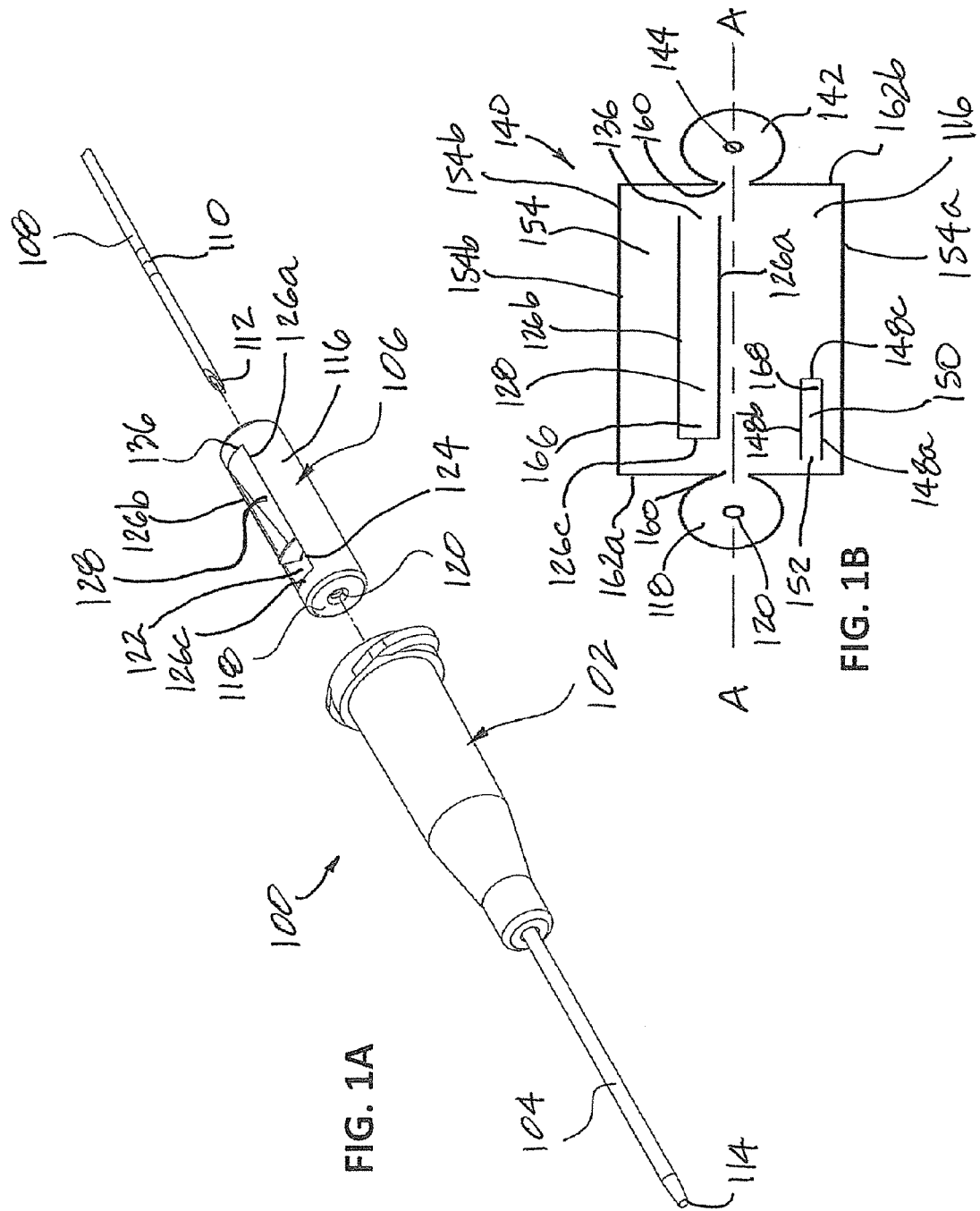
FIG. 1A is an exploded perspective view of a catheter assembly in accordance with aspects of the present disclosure.
FIG. 1B is a plan view of a stamped metal sheet usable to form the needle guard of FIG. 1.
Figure 2:
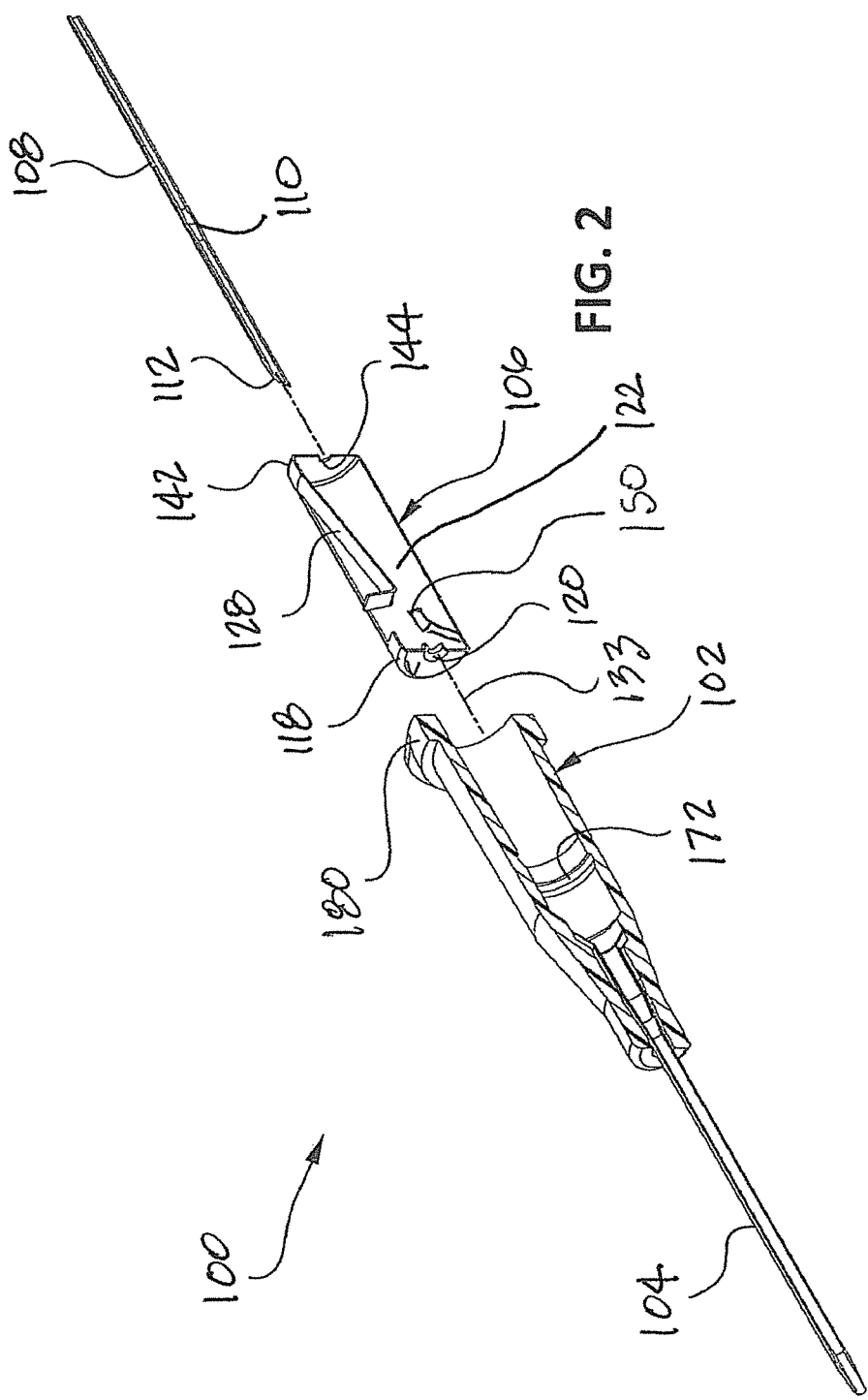
FIG. 2 is an exploded cross-sectional view of the catheter assembly of FIG. 1.

With reference now to FIGS. 1A and 2, an intravenous catheter assembly 100 is shown in exploded view in accordance with aspects of the present disclosure. The assembly includes a catheter hub 102 with a catheter tube 104, a tip protector or needle guard 106, and a needle 108 attached to a needle hub (not shown) with said needle comprising a change in profile 110 located proximally of a needle tip 112. In some examples, the change in profile can be a crimp, which has a recessed section and an enlarged section, or a material build up so that a cross-section of the change profile 110 differs in shape and/or geometry than the nominal diameter section of the needle. In a ready to use position, the needle guard 106 is disposed in the interior cavity of the catheter hub 102 and needle 116 projects through the needle guard 106, the catheter hub 102, and the catheter tube 104 such that the tip 112 extends distally of the distal opening 114 of the catheter tube. Further in the ready to use position, the nose section of the needle hub projects into the catheter hub and frictionally engages with the female Luer of the catheter hub. If the needle guard 106 is sized so that the proximal end of the needle guard is roughly flushed with the proximal end edge of the catheter hub, then the nose of the needle hub does not project into the catheter hub. In that situation, the needle hub can engage to the outside of the catheter hub.

In one exemplary embodiment, the needle guard 106 has a body 116 that is generally cylindrical in shape and has a distal wall 118 with an opening 120 and an opposing proximal wall with an opening (FIG. 2). The needle 108 projects through the two openings of the needle guard in a ready to use position, which defines a lengthwise axis 133. The body 116 has an elongated side opening 124 formed by three generally linear cuts 126a, 126b, 126c. The body is left intact at the fixed end 136 opposite the short cut 126c to form a deflectable arm 128, also sometimes referred to as a biasing arm, which is folded or bent inwardly towards the interior cavity 122 of the needle guard. The biasing arm 128 may be referred to as a biasing member resembling a leaf spring that springs, pivots and/or deflects at the fixed end 136.

With reference now to FIG. 1B, a stamped metal sheet 140 is shown for forming the needle guard 106 of FIG. 1A. For example, one or more stamping dies may be used to stamp a thin stainless steel sheet to form the stamped metal sheet 140 shown. The stamped metal sheet 140 has two generally cylindrical tabs 118, 142 for forming the distal wall and the proximal wall of the needle guard witch each tab comprising an opening 120, 144. In one example, the proximal opening 144 is smaller than the distal opening 120. The proximal opening is smaller than the largest cross-sectional dimension of the change in profile 110 on the needle to ensure engagement between the two upon retraction of the needle from the catheter hub and the catheter tube following successful venipuncture.

A first tab that functions as a first leaf spring is formed with three continuous cuts 126a, 126b, 126c for forming the first biasing arm 128. A second tab that functions as a second leaf spring is formed with a second set of three continuous cuts 148a, 148b, 148c for forming a second biasing arm 150, which has a fixed end 152 attached to the material layer 154 of the body 116. Thus, the stamped metal sheet 140 has at least two tabs for forming two biasing members or arms when rolled to form the needle guard of FIG. 1A. In other examples, additional tabs for forming additional arms may be incorporated. The locations of the two arms 128 150 relative to the lengthwise axis A-A of the stamped sheet 140 can vary relative to the two side edges 154a, 154b and relative to one another. The spacing of the two tabs relative to one another will determine the respective positions of the two biasing members 128, 150 upon rolling the stamped metal sheet 140 into the cylindrical housing shown in FIG. 1A. For example, the two arms can be located about 180 degrees from one another or some increment that is not less than about 10 degrees from one another measured along an arc circle of the rolled body. Similarly, the locations of the two tabs 118, 142 relative to the lengthwise axis A-A and the two edges 154a, 154b can vary. As the two tabs 118, 142 are simply folded downward towards the center of the axis of the safety casing or guard at their respective attached ends 160 after the body 116 is rolled to form the two end walls, i.e., the proximal wall and the distal wall of the needle guard, they can be more freely positioned within a greater distance from the lengthwise axis along the two end edges 162a, 162b. Thus, the location of the attached ends 160 of the two tabs can vary along the end edges 162a, 162b and can be folded from different positions from the two end edges to form the two end walls on the needle guard.

In one example, the two tabs 128, 150 are manipulated before the body 116 is formed, such as by rolling into a cylindrical housing. As further discussed below, the two arms 128, 150 have a bent at the respective fixed ends 136, 152 and near the respective short cuts 126c, 148c to form finger elements. In an example, the two fixed ends 136, 152 of the two arms are aligned opposite one another so that each is close to a respective end edge 162a, 162b of the stamped metal sheet 140. The two free ends 166, 168 of the two arms 128, 150 point in opposite directions and are both inwardly positioned such that the presence of the needle biases the two arms outwardly away from the lengthwise axis 133 of the guard. After the stamped metal sheet 140 is rolled and the two tabs 118, 142 folded, the seams where the tabs 118, 142 fold against the end edges 162a, 162b and the seam at the two side edges 154a, 154b are welded, such as by laser welding, tack welding, or other welding means. In some examples, the stamped metal sheet 140 has one or more openings formed on the body 116 for inspection inside the interior cavity of the needle guard and/or for use to facilitate assembly of the needle guard onto a needle.

In one exemplary embodiment the catheter hub 102 includes an internal diameter at least slightly larger than an outer diameter of the body 116 of the needle guard to receive the guard in a ready to use position. In some embodiments, the body 116 of the needle guard is pressed into the interior cavity of the catheter hub and forms a seal with the interior surface of the catheter hub. For example, the distal end of the needle guard can be pressed fit into the catheter hub to form a seal along a circumference of the body of the guard closer to the distal wall 118 than the proximal wall 142. In some embodiments, for example, the guard 106 or catheter hub 102 includes grooves, ridges or an otherwise textured outer surface to facilitate a secure grip.

Absorbable material can be also added to the internal space of the safety casing, such as to the interior cavity 122 of the needle guard 106, so as to prevent blood exposure for a needle having a notch opening near the needle tip or the blood residual in the inner bore of the cannula. For example, a blood coagulating agent may be added to the interior cavity of the needle guard to reduce potential dripping of blood particles.

In some embodiments, as discussed in more detail below, the catheter hub 102 includes a guard engagement section 172 (FIG. 2), which can be an aperture, shoulder, or recess or other securing feature to facilitate securing the needle guard 106 to the catheter hub 102. In an embodiment, the guard engagement section 172 is an annular groove or an annular recess. In another embodiment, the annular groove comprises a section of a first diameter located adjacent an area of a second diameter, which is smaller than the first diameter. A finger element or member of the needle guard is configured to engage the guard engagement section 172, thereby securing the needle guard to the catheter hub 102 so that the guard remains with the catheter hub during retraction of the needle following successful venipuncture until the finger element of the first biasing member 128 releases from the guard engagement section 172 of the catheter hub, at such time the needle guard is secured to the needle and is withdrawn with the needle.

FIG. 3 shows a cross-section side view of the catheter assembly 100 of FIG. 1A in a ready to use position, shown without a needle hub, which can abut the proximal end surface 178 of the catheter hub or grip the exterior of the catheter hub, such as around the external threads 180. The needle guard 106 is shown with the first arm 128 bent inwardly towards the needle 108. The first arm 128 also has a bend 182 near the distal end of the arm to form a finger element 184 having a tip 186. When the needle is inserted into the needle guard as shown and through the proximal and distal openings 144, 120, the needle biases the first arm 128 outwardly so that the tip 186 engages the guard engagement section 172 of the catheter hub. More specifically, the needle biases the finger including the tip outwardly so that the tip 186 emerges out of the elongated opening 124 defined by the three cut sections 126a, 126b, 126c (FIG. 1B) to engage the guard engagement section 172 of the catheter hub. This fixes the needle guard to the catheter hub so that during retraction of the needle away from the catheter tube and until the needle tip moves proximally of the finger 184, at which time the tip 186 and finger 184 move radially inwardly, as the needle no longer biases the arm outwardly, to separate from the guard engagement section 172. Further retraction of the needle causes the change in profile 110 on the needle to engage the proximal opening 144 on the proximal wall 142 and pulls the proximal wall out with the needle, which effectively pulls the entire needle guard out with the needle, as further discussed below with reference to FIG. 4.

FIG. 3 also shows the second arm 150 bent inwardly into the interior cavity 122 of the needle guard at the fixed end 152. The second arm 150 further has a second bend 190 forming a finger section 192. The second arm 150 can optionally be provided with a kink or folded section 196 between the finger 192 and the fixed end 152. As shown, the folded section 196 is generally V-shape. The folded section 196, if provided, may provide a means for controlling the length of the second arm from the fixed end 152 to the bend 190, which forms the finger. The folded section 196, if provided, can also influence the flexing of the second arm 150 and the second finger 192 by the needle.

To install the needle through the openings 120, 144 at the proximal and distal walls 118, 142, the butt end of the needle, opposite the needle tip, may be inserted through the distal opening 120 first, which automatically deflects the second arm 150 radially outwardly. To push the butt end past the first arm 128, a tool may be used to lift the first arm 128 outwardly from the proximal side of the needle guard to provide clearance for advancing the needle through the proximal opening 144. For example, an installation pin may be inserted through the proximal opening 144 of the proximal wall 142 to lift the first arm and then subsequently removed so that the butt end of the needle can be placed through the proximal opening 144. The needle and needle guard are then pushed into the interior cavity of the catheter hub and the needle through the catheter tube with the needle tip extending distally past the catheter tube opening. The flexibility of the finger and arm will allow the guard and needle to be pushed inside the catheter hub.

Thus, an aspect of the present disclosure includes a needle that biases at least two biasing arms or members on a needle guard in a ready position. The at least two biasing arms are spaced apart from one another. As shown, the two spaced apart arms, which have fingers located at respective ends thereof, have fixed ends that are located on opposite ends of the guard body, close to the proximal wall and distal wall, respectively. For example, one arm has a fixed end nearer the proximal wall while the other arm has a fixed end nearer the distal wall. The fixed end of each arm, which is attached and not freely movable, is located opposite a free end, which is not attached and is freely deflectable. In an example, a finger is located at each free end and each finger is attached to the arm by way of a bend.

The manner in which the needle guard 106 is activated to cover the needle tip 112 is further shown with reference to FIG. 4. As the needle 108 is withdrawn from the catheter tube 104 and the then through the catheter hub 102 following successful catheterization, as shown by the direction of the arrow 200, the needle slides against the surfaces of the biasing members or arms 128, 150, at or near the intersection between the respective arm and finger. As the needle tip 112 of the needle 108 moves proximally of the second biasing member 150, the second biasing member deflects radially inwardly so that at least most of the arm and the finger 192 remain in the interior cavity 122 of the needle guard. As shown, the second biasing arm 150 is sized with a length so that the arm blocks the distal opening 120 of the needle guard to prevent the needle tip 112 from re-emerging out through the distal opening. The finger can also block the distal opening depending on the extent of the bend between the finger and the arm. For example, the second arm can be unbent and therefore only the second atm blocks the distal opening. As the needle tip 112 continues to move proximally, the bias of the first arm 128 causes the needle 108 to deflect radially off the longitudinal axis 133 defined by the two openings 120, 144 of the needle guard. As the first biasing arm 128 moves radially inward into the interior cavity of the needle guard, the tip 186 at the end of the finger 184 moves out of the guard engagement segment 172 of the catheter hub. Further retraction of the needle causes the change in profile 110 to engage the proximal opening 144 which then moves the proximal wall 142 in the same proximal direction out of the catheter hub 102. In some embodiments, the arm may be coated with a low friction material, such as plastic, to reduce friction between the needle and the biasing members 128, 150. Thus, in the first position or ready position of the needle guard as shown in FIG. 3, at least one of the two biasing members, such as the second arm 150, is biased by the needle shaft and wherein in the second position the at least one of the two biasing members, again the second arm 150, is not biased by the needle shaft and covers at least part of the distal opening of the distal wall to prevent the needle tip from re-emerging out the distal opening.

Thus, an aspect of the present disclosure is understood to include a catheter assembly comprising a needle guard located inside an interior cavity of a catheter hub, said needle guard comprising a first biasing arm or member and a second biasing arm or member that are biased radially outwardly from a lengthwise axis 133 of the needle guard by a needle. At least one of the arms has a finger and a tip and wherein the tip is pushed by the needle into engagement with a guard engagement member formed in the interior cavity of the catheter hub. The guard is removable from the catheter hub when the needle tip moves proximally of a bend on the second arm and proximally of a bend on the first arm to allow the tip to separate from the guard engagement section. A further aspect of the present disclosure includes a provision for covering a distal opening to prevent the needle from re-emerging out through the distal opening after retraction of the needle tip into the interior cavity of the needle guard. In a particular example, the second biasing arm or member deflects radially when no longer biased by the needle to cover the distal opening. In an example, the first biasing arm has a fixed end located closer to the proximal wall than the distal wall and the second biasing arm as a fixed end located closer to the distal wall than the proximal wall. A still further feature of the present disclosure is understood to include tilting the needle from the lengthwise axis upon moving proximally of the bend of the second arm. In an example, the first arm biases inwardly to tilt the needle away from the lengthwise axis. Further retraction of the needle causes the change in profile to engage the proximal opening on the proximal wall and retracts the needle guard away from the catheter hub.

At this point, any attempt to reverse direction of the needle tip would be blocked from exiting the needle guard 106 by the combination of the deflection caused by the first biasing member 128 and the blocking of the distal opening 120 by the second biasing member 150. In this manner, the needle tip 112 may be effectively confined within the hollow interior region 122 of the needle guard 106 to prevent inadvertent needle stick with the needle tip.

Thus, an aspect of the present disclosure is directed to a needle safety device comprising a needle connected to a needle hub, said needle comprising a needle shaft and a change in profile near a needle tip; and a needle guard having a body defining an interior cavity, a distal wall having a distal opening, and a proximal wall having a proximal opening having the needle shaft passing through both the distal opening and the proximal opening in a ready to use position in which the needle tip is exposed; wherein the change in profile has a larger cross-sectional dimension than a dimension of the proximal opening for engaging the proximal opening in a protective position; wherein the needle guard comprises at least two biasing members and wherein at least one of the two biasing members has a first position when the needle tip is exposed and a second position when the needle tip is located inside the interior cavity of the needle guard; and wherein in the first position the at least one of the two biasing members is biased by the needle shaft and wherein in the second position the at least one of the two biasing members is not biased by the needle shaft and covers at least part of the distal opening of the distal wall to prevent the needle tip from re-emerging out the distal opening.

An alternate needle guard 230 embodiment usable with a catheter assembly is shown in FIG. 5. As shown, the needle guard 230 is located inside an interior cavity of a catheter hub 102, which may be similar to the catheter hub discussed elsewhere herein. In an example, the alternate needle guard 230 comprises a body 232, a proximal wall 234 with a proximal opening 236 having a needle 108 with a change in profile located proximally of a needle tip disposed therethrough, and a plurality of biasing fingers or members 238 with at least one of the biasing members being an extended finger 240. In an example, the plurality of fingers each with a respective first length and an extended finger having a second length and wherein the second length is longer than each of the first lengths. The tips of the plurality of fingers 238 and at least part of the extended finger 240 define a distal wall 243 with a distal opening 244, which is dynamic and can change shape and/or size.

The fingers 238 are deflectable to enable the needle to pass therethrough, such as by pushing the butt end of the needle into the needle guard through the distal opening 244, which causes the fingers to deflect to accept the needle. The at least one extended finger 240 is longer so that part of the extended finger, rather than the distal end edge of the extended finger 240, rests against the side of the needle, as shown in FIG. 5. Thus, when the needle tip moves proximally into the interior cavity 250 of the needle guard following successful venipuncture to remove the needle from the catheter hub and the catheter tube, as shown in FIG. 6, the plurality of fingers 238 straighten, such as being less deflected by the needle. As the fingers 238 straighten in a protective position, the size of the distal opening 244 decreases. The distal opening 244 can also change shape as the contour of the distal ends of the fingers without the needle in the protective position can appear different than when the needle is located therein. Because the at least one extended finger 240 is longer than the other fingers 238, it straightens to cover all or at least part of the distal opening 244, which prevents the needle tip from re-emerging out through the distal opening of the needle guard 230. The change in profile on the needle subsequently engages the proximal opening 236, or the opening on the casing as further discussed below, to then retract the needle guard away from the catheter hub. Thus, the needle safety device is understood to include at least two biasing members and wherein in the first position at least one of the two biasing members, such as the extended finger 240, is biased by the needle shaft and wherein in the second position the at least one of the two biasing members is not biased by the needle shaft and covers at least part of the distal opening of the distal wall to prevent the needle tip from re-emerging out the distal opening.

In an example, the extended finger 240 is provided with additional bends. For example, rather than a single bend so that the extended finger 240 rests against a side of the needle 108 as shown in FIG. 5, that portion that rests on the needle can be provided with a "v" shaped, "n" shaped or other shaped configurations so that less of the extended finger 240 surface contacts the needle at the ready position shown in FIG. 5. When the various bends are provided with the extended finger 240, its effective length can be reduced due to the bends and the extended finger contacts the needle at one or more points rather than along an extended length. This will reduce drag during retraction of the needle following successful venipuncture and can provide added biasing function created or produced by the bends.

In an alternative embodiment, the fingers 238 and the at least one extended finger 240 as well as the arms to which the fingers are attached move radially inwardly when the needle is no longer located in the distal opening. This also causes the distal opening 244 to change in shape and/or size. In yet another example, the angle or angles to which the fingers are attached to the arms are fixed and only the arms move radially inwardly when the needle is no longer located in the distal opening 244. This also causes the distal opening 244 to change in shape and/or size.

Thus, an aspect of the present disclosure is understood to include a catheter assembly comprising a catheter hub with a catheter tube, a needle hub with a needle projecting through the catheter tube in a ready to use position, and a needle guard located inside the interior cavity of the catheter hub. In an example, the needle guard comprises a body section comprising a proximal wall with a proximal opening and a plurality of fingers with at least one extended finger defining a dynamic distal opening having the needle positioned in both the proximal opening and the dynamic distal opening in a ready to use position. The distal opening has a first size when in the ready to use position and a second size, which differs from the first size, when the needle is displaced from the distal opening. Further, the extended finger, which may be considered a biasing member, at least partially covers the distal opening when the needle is displaced from the distal opening.

Also shown in FIG. 5 is a casing 260 surrounding the needle guard 230. In an example, the casing is a plastic housing placed over the needle guard. In another example, the casing is an elastomer that is stretched to receive the needle guard. In yet another example, the casing is made from multi-piece rigid or semi-rigid plastic that is placed over the needle guard 230 and then subsequently secured together, such as by gluing or welding. The casing 260 comprises a projection 262 for engaging the guard engagement section 172 formed with the catheter hub 102. The combination needle guard 230 and casing 260 may be referred to as a guard device 270. The casing has a distal opening and a proximal opening. The proximal opening can be sized larger than or smaller than the change in profile on the needle to engage the change in profile. The engagement between the projection 262 and the guard engagement section 172 allows the guard device 270 to be secured to the catheter hub 102 in the ready to use position and during retraction of the needle following successful venipuncture.

In an alternative embodiment, the casing 260 for the guard device 270 of FIG. 5 may be omitted and the needle guard 230 provided with an engagement feature for engaging the catheter hub in the ready to use position and during retraction of the needle. In an example, one or more of the fingers 238, which may be referred to as biasing members, may be formed with an engagement feature, such as bent to include a folded section or a projection, to engage the guard engagement section 172 of the catheter hub 102.

In another example, the needle guard 230 is molded from a plastic material. The plastic guard can be molded with multiple fingers with different lengths. While the plastic is still warm following injection molding, the fingers can be bent over to form the distal wall 243 with a distal opening 244 as shown in FIG. 5. Alternatively or in addition thereto, the plastic guard may be heated before and during bending to shape the distal wall and distal opening.

With reference now to FIG. 5A, a stamped metal sheet 280 is shown, which is usable to form the needle guard 230 of FIG. 5. In the example shown, the stamped metal sheet 280 has a body 232 having a plurality of slits or cuts 282 to form a plurality of independently movable elongated tabs 284 with ends that form a finger end edge 289, which is generally along a straight line with some variation in tolerance being acceptable. The elongated tabs 284 can be bent to form the fingers or biasing members 238 shown in FIG. 5. The stamped metal sheet 280 further includes at least one extended elongated tab 286 for forming the extended finger 240 of FIG. 5, which is longer than the elongated tabs 284 and has a length that extends beyond the finger end edge 289. The extended elongated tab 286 can be located anywhere along the finger end edge 289, such as closer to one of the side edges 294a, 294b. The length of the cuts 282 can vary and the spacing between cuts can vary depending the size of elongated tabs desired, which can affect the flexibility and stiffness of the fingers. Additional extended elongated tabs can also be provided so that the longer length of the additional extended elongated tabs can be used to form a projection for engaging the guard engagement section of the catheter hub. A curved tab 290 with an opening 236 is provided at the end edge 292 of the stamped metal sheet 280. The curved tab 290 may be folded to form the proximal wall 234 of the guard of FIG. 5.

To form the needle guard 230 of FIG. 5, the elongated tabs 284 and the extended elongated tab 286 are bent to form fingers. If used without a casing, one or more extended elongated tabs are folded to cooperatively form an outward projection to engage the guard engagement section of the catheter hub. The body 232 of the stamped metal sheet 280 is then rolled so that the two side edges 294a, 294 come together to form a generally cylindrical structure. If used without a casing, the seam formed between the two side edges 294a, 294b may be welded or tack welded. If used with a casing, the seam between the two side edges 294a, 294b may be welded or left un-welded and then placed inside the casing.

FIG. 6 shows the device of FIG. 5 when the needle 108 is retracted in a proximal direction until the needle tip 112 enters the interior space or cavity 250 of the needle guard 230. As shown, the various tabs 284 are deflected inwardly when no longer held or when no longer biased outwardly by the presence of the needle in the distal opening 244. This allows the projection 262 to separate from the guard engagement section 172 of the catheter hub 102. As shown, the distal opening 244 collapses in size and the extended finger 240 deflecting to block at least part of or all of the distal opening 244. This prevents the needle tip 112 from moving in the distal direction to re-emerge out the distal opening 244.

FIG. 6 also shows the change in profile 110 moving against the proximal opening 236 of the needle guard. As the change in profile 110 is larger than the proximal opening, further movement in the proximal direction will cause the guard device 270 to move out of the catheter hub with the needle.

Thus, an aspect of the present disclosure is directed to a needle safety device comprising a needle connected to a needle hub, said needle comprising a needle shaft and a change in profile near a needle tip; and a needle guard having a body defining an interior cavity, a distal wall having a distal opening, and a proximal wall having a proximal opening having the needle shaft passing through both the distal opening and the proximal opening in a ready to use position in which the needle tip is exposed; wherein the change in profile has a larger cross-sectional dimension than a dimension of the proximal opening for engaging the proximal opening in a protective position; wherein the needle guard comprises at least two biasing members and wherein at least one of the two biasing members has a first position when the needle tip is exposed and a second position when the needle tip is located inside the interior cavity of the needle guard; and wherein in the first position the at least one of the two biasing members is biased by the needle shaft and wherein in the second position the at least one of the two biasing members is not biased by the needle shaft and covers at least part of the distal opening of the distal wall to prevent the needle tip from re-emerging out the distal opening.

With reference now to FIG. 7, an alternative stamped metal sheet 300 for forming the needle guard 230 of FIGS. 5 and 6 is shown. The stamped metal sheet 300 comprises a generally round body 232 having a plurality of elongated tabs 284 extending from the body, including at least one extended elongated tab 286 for forming the extended finger 240 on the needle guard, and a perimeter defining an opening 236. In another example, the opening 236 is formed after the stamped metal sheet is been drawn through a die or several dies. The width of the various extended tabs 284, the spacing between the extended tabs 284, and the number of extended tabs 284 can vary depending on how fine or coarse the intended needle guard is desired to embody. For example, the larger the spacing or gap between the extended tabs 284 will cause noticeable gaps between the arms and the fingers of the formed needle guard. The longer the extended tabs will result in independently movable arms that have bases located closer to the proximal wall of the formed needle guard compared to extended tabs that are relatively shorter in lengths. As shown, the extended tabs 284 can also have tapered side edges 310a, 310b.

The stamped metal sheet 300 may be turned into a needle guard 230 through a drawing process or a progressive stamping process. A die or multiple dies may be used in a drawing process to shape the blank into a cylindrical shape by thinning the wall of the stamped piece. The die or dies used to shape the blank may have different shapes and contours for forming a different shaped guard. Generally speaking, the shaped body section of the needle guard can be described as a negative image of the die or dies. A great deal of force is used to plastically deform a blank or work piece. In one example, a hydraulic actuated press is used to supply the working pressure. In other examples, a gear driven press or a mechanical press may be used to supply the working pressure. Unless the context indicates otherwise, drawing and progressive stamping for purposes of the present disclosure are used synonymously.

After securing the sheet of FIG. 7 through a stamping process, the sheet 300 is drawn near the mid-section 312 of the body 302, as shown in FIG. 8(a). The extended tabs 284 are left dangling during this part of the process. Note also that the sequence of process shown in FIGS. 8(a)-8(d) is simplified with two arms only although it is understood that the process starts with the stamped sheet 300 of FIG. 7, which has multiple extended tabs 304 for forming a needle guard 230 with multiple fingers and a variable distal opening of FIGS. 5 and 6. The figures are also not shown to scale.

The sheet 300 is drawn deeper into a die to create an elongated body as shown in FIG. 8(b). At this point of the process, a proximal opening 236 may be formed on the intermediate product.

The extended tabs 284 are then bent inwards as shown in FIG. 8(c). The at least one elongated extended tab 286 may be bent first and may include multiple bends as discussed above to form an extended finger 240 with a simple bend or with multiple bends. The remaining extended tabs 284 are then bent inwards. The extended tabs 284 are further manipulated by bending them inwards into the interior cavity 250 of the guard body. In the process, a distal wall 243 with a dynamic distal opening 244 is formed, as shown in FIG. 8(d). Advantageously, the guard of FIGS. 7-8(d) does not require any welding.

Figure 9:
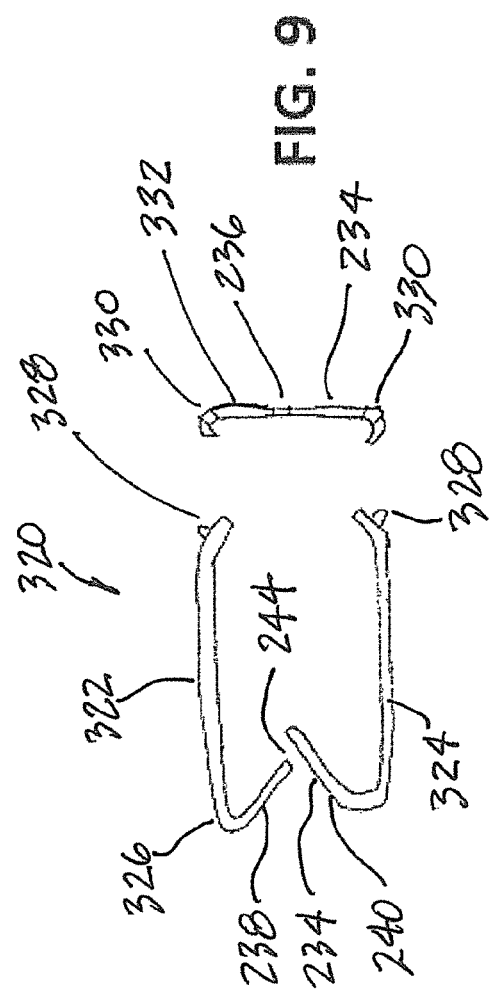
FIG. 9 is an alternative needle guard made from at least two separately formed pieces that are subsequently combined or joined to form a completed needle guard.

With reference now to FIG. 9, an alternative needle guard 320 comprising a body 322 having a plurality of flexible fingers 238 and at least one extended finger 240 is shown. The body 322 can optionally include independently movable arms 324 that terminate with the independently movable fingers 238, 240 or the body can instead be formed as a solid structure at the way to the distal edge or joint 326 and only the fingers 238, 240 are independently movable. In one example, the guard 320 is made from plastic, such as by plastic injection. While the plastic is still warm following injection molding, the fingers can be bent over to form the distal wall 243 with a distal opening 244 as shown for the guard of FIG. 5. Alternatively or in addition thereto, the plastic guard may be heated before and during bending of the fingers to shape the distal wall and distal opening. The guard body 322 is provided with an engagement means, such as two or more projections 328, for engaging corresponding recesses 330 formed on a rear plate 332. In alternative embodiments, locations of the projections 328 and the recesses 330 can reverse. The rear plate 332 is therefore configured to snap fit with the guard body 322 to form a needle guard 320 having a distal wall 234 with a plurality of independently movable fingers 238 and at least one extended finger for blocking the distal opening 244, similar to the needle guard discussed above with reference to FIGS. 5 and 6. The rear plate 332 therefore functions as a proximal wall 234 for the needle guard 320 having a perimeter defining a proximal opening 236. In one example, the rear plate 332 is made from a metal material. In another example, the rear plate 332 is made from a hard plastic. Advantageously, the guard of FIG. 9 does not require any welding. In a less preferred embodiment, the guard body 322 is formed from multiple pieces that are then attached together, such as by heat welding or by gluing.

Figure 10:
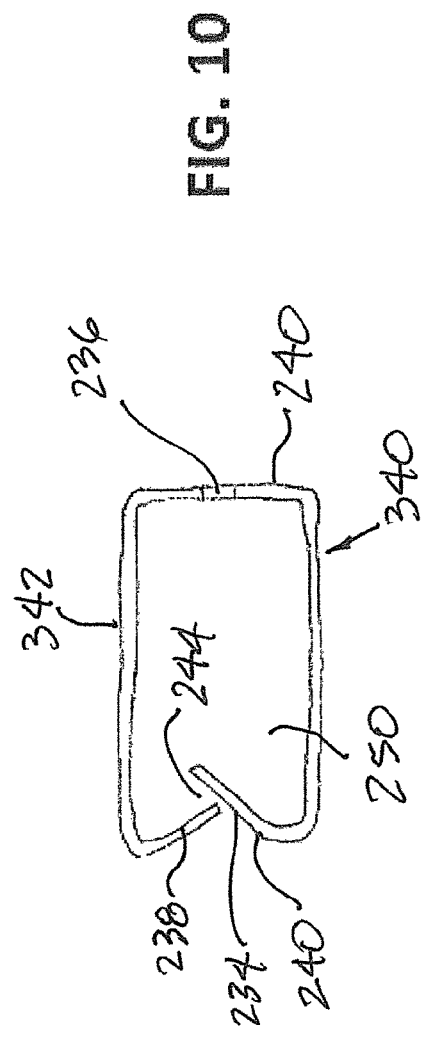
FIG. 10 is yet another alternative needle guard made from plastic.

FIG. 10 shows another needle guard 340 provided in accordance with further aspects of the present devices, systems, and methods. The needle guard 340 comprises a body 342 comprising a proximal wall 234 having a proximal opening 236 and a distal wall 234 having a distal opening 244. The guard 340 of the present embodiment is similar to the needle guard 230 of FIGS. 5 and 6 except it is made from plastic, such as by plastic injection molding. Thus, the present needle guard comprises a plurality of independently movable fingers 28 and at least one extended finger 240 for blocking the distal opening 244, as discussed elsewhere herein. The needle guard may be molded with the body 342, the proximal wall 234, and with the independently movable fingers 238 initially in an un-bent state, such as being generally aligned with the contour of the body. Following the molding process, the fingers are bent into the interior cavity 250 of the needle guard. For example, the plastic guard may be heated at the fingers before and during bending of the fingers to shape the distal wall 234 and distal opening 244. The proximal wall 234 may include a metal insert, such as a washer, to strengthen the proximal opening 236. When pulled by a change in profile of a needle, the metal insert will increase the pulling force required to pull the change in profile through the opening. Advantageously, the guard of FIG. 10 does not require any welding. In a less preferred embodiment, the guard body 342 is formed from multiple pieces that are then attached together, such as by heat welding or by gluing.

Method of making and method of using needle safety assemblies, needle guards, and guard devices described elsewhere herein are also contemplated.

Further, while the needle guards described herein are with reference to a catheter assembly, the needle guards may be used with other needle types without a catheter hub. For example, the needle guards described herein may be placed over a hypodermic needle and then manually slid over the needle tip following an injection to cover the used needle tip.

Although limited embodiments of needle safety assemblies and their components have been specifically described and illustrated herein, many modifications and variations will be apparent to those skilled in the art. For example, the various protective shields may incorporate translucent materials allowing a user to view the needle after the needle shield is released, etc. Furthermore, it is understood and contemplated that features specifically discussed for one needle safety device embodiment may be adopted for inclusion with another needle safety device embodiment, provided the functions are compatible. For example, a leg extension may be used in another embodiment shown with unequal length biasing members. Further, while the needle guards described are typically positioned inside a catheter hub, the guard may be placed outside the catheter hub, such as in a third housing that differs from the catheter hub and the needle hub. The third hub can have portions that engage the catheter hub in a ready to use position and during retraction of the needle following successful venipuncture. Another example includes elements that allow a user to detect flashback. Accordingly, it is to be understood that the needle safety assemblies and their components constructed according to principles of the disclosed devices, systems, and methods may be embodied other than as specifically described herein. The disclosure is also defined in the following claims.

What is claimed is:

1. A needle safety device comprising:
   a needle connected to a needle hub, said needle comprising a needle shaft and a change in profile near a needle tip; and
   a needle guard having a body defining an interior cavity, a distal wall comprising a distally facing wall surface and a proximally facing wall surface at a distal end of the body having a distal opening, and a proximal wall at a proximal end having a proximal opening having the needle shaft passing through both the distal opening and the proximal opening in a ready to use position in which the needle tip is exposed; wherein the change in profile has a larger cross-sectional dimension than a dimension of the proximal opening for engaging the proximal opening in a protective position;

wherein the needle guard comprises at least two biasing members including a first biasing member and a second biasing member and wherein the second biasing member is located closer to the distal end than the proximal end, the second biasing member has a first position when the needle tip is exposed and a second position when the needle tip is located inside the interior cavity of the needle guard;

wherein in the first position the second biasing member is biased by the needle shaft and wherein in the second position the second biasing member is not biased by the needle shaft and covers at least part of the distal opening of the distal wall to prevent the needle tip from re-emerging out the distal opening; and wherein the second biasing member has a free end and a fixed end and wherein the fixed end of the second biasing member is located closer to the distal end than the free end is to the distal end.

2. The device of claim 1, wherein the second biasing member has an intermediate bent section.

3. The device of claim 1, further comprising a catheter hub and a catheter tube and wherein the needle guard is located in an interior cavity of the catheter hub.

4. The device of claim 2, wherein the bent section has a V-shape.

5. The device of claim 1, wherein the first biasing member comprise a first biasing arm and wherein the first biasing arm has a fixed end and a free end and wherein the fixed end of the first biasing arm is located closer to the proximal end than the free end is to the proximal end.

6. The device of claim 1, wherein a plurality of fingers define the distal wall with the distal opening and wherein the distal opening is a dynamic opening that changes size depending on the position of the needle shaft.

7. The device of claim 1, wherein the distal opening is circumscribed by a plurality of independently movable fingers each with a fixed end and a free end and wherein the fixed end is located closer to the distal end than the free end.

8. The device of claim 1, wherein the body is made from a plastic material or from a stamped metal sheet.

9. The device of claim 1, wherein the needle guard is rolled from a stamped metal sheet and wherein the stamped metal sheet has a plurality of cuts or slits for forming the biasing members.

10. A method of using the needle safety device of claim 1, further comprising moving the needle guard and the needle relative to another so that the needle guard covers the needle tip.

* * * * *